United States Patent [19]

Goetz

[11] 4,046,667

[45] Sept. 6, 1977

[54] MICROELECTROPHORESIS APPARATUS

[75] Inventor: Philip J. Goetz, Pleasantville, N.Y.

[73] Assignee: Pen Kem, Inc., Croton-On-Hudson, N.Y.

[21] Appl. No.: 627,299

[22] Filed: Oct. 30, 1975

[51] Int. Cl.² .................... G01N 27/26; G01N 27/28
[52] U.S. Cl. .......................... 204/299 R; 204/180 R
[58] Field of Search .......................... 204/299, 180 R; 356/102, 103

[56] References Cited

U.S. PATENT DOCUMENTS

| 3,454,487 | 7/1969 | Riddick | 204/299 |
| 3,764,512 | 10/1973 | Greenwood et al. | 204/299 |
| 3,793,180 | 2/1974 | Flower et al. | 204/299 |

*Primary Examiner*—Arthur C. Prescott

[57] ABSTRACT

Microelectrophoresis apparatus is provided comprising an electrophoresis chamber, circuit means for impressing a voltage across the chamber, means for generating a light beam to illuminate a portion of the chamber, and a microscope including an objective lens system and an eyepiece for viewing illuminated particles migrating relative to a suspending medium within the chamber under the influence of the applied voltage. Disposed within the microscope between the objective lens system and the eyepiece i.e., internally of the microscope, is a movable optical prism driven by a galvanometer, the drive circuit of which includes an adjustable potentiometer for controlling the rate and direction of movement of the optical prism. Circuit means connected to the galvanometer drive circuit and the circuit applying the voltage potential across the chamber is adapted to develop a signal proportional to the electrophoretic mobility or zeta potential of the migrating particles in the medium in the chamber when the rate of movement of the optical prism is adjusted such that it cancels the transfer velocity of the migrating particles and the particles appear stationary when observed through the eyepiece of the microscope.

30 Claims, 8 Drawing Figures

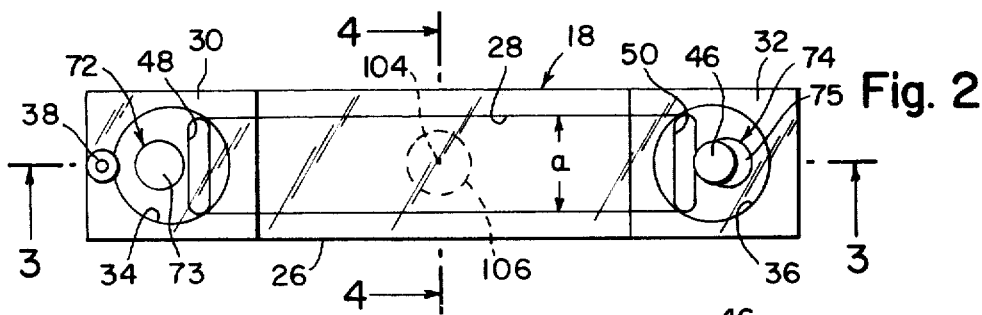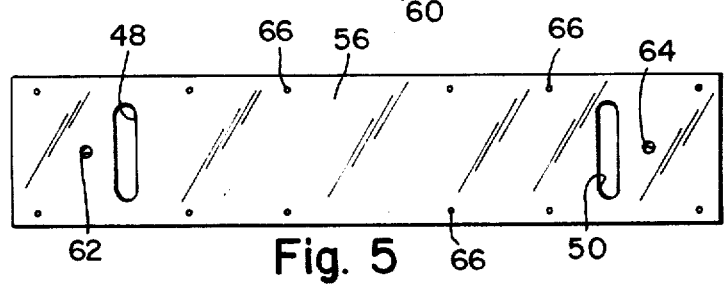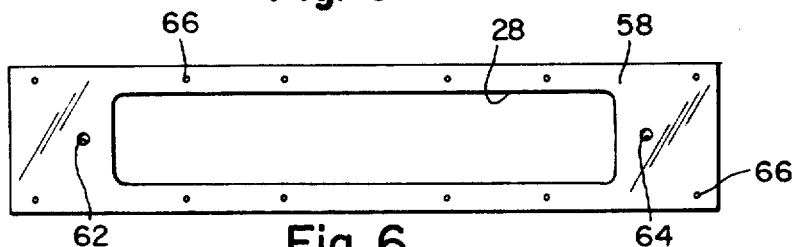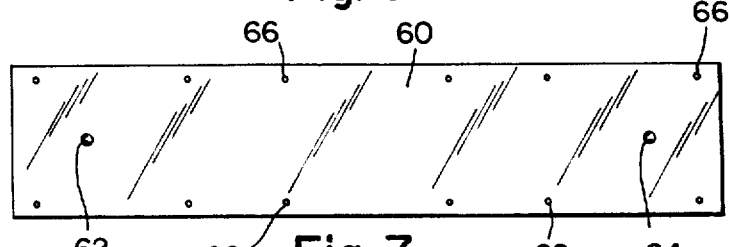

MICROELECTROPHORESIS APPARATUS

The present invention relates generally to electrophoresis apparatus, and more specifically to microelectrophoresis apparatus for measuring the zeta potential or electrophoretic mobility of particles suspended in a bulk medium e.g., colloids suspended in a liquid.

As is now well documented in the art, the term "zeta potential" refers to the net or effective charge on a particle, usually expressed in millivolts, produced by the interaction of the particle and the bulk medium in which it is suspended. As an example, most natural colloids suspended in an aqueous solution exhibit a net electronegative charge usually within the range of $-15$ to $-30$ mv.

The stability of a particle suspended in a bulk medium is directly related to the net effective charge on the particle or its zeta potential. Stable particles remain separate and distinct (i.e., dispersed) whereas unstable particles tend to agglomerate and eventually precipitate out of the suspending medium or solution. Generally speaking, the higher the net effective charge or zeta potential the more stable the system since if the charge on the particles is high they repel one another and remain dispersed. In some cases it is desirable to maximize the particle charge in order to achieve greater stability such as in the manufacture of paints, pharmaceuticals, cosmetics, etc. On the other hand, it is sometimes necessary to minimize the charge or zeta potential of the suspended particles as for example, in treating waste and sewage water, or during the manufacture of paper. In all cases it thus becomes extremely desirable to be able to accurately and efficiently measure the zeta potential of particles suspended in a bulk medium.

The classical technique employed in measuring the zeta potential of suspended particles consists of impressing a D.C. voltage across a sample of the bulk suspending medium via a pair of spaced electrodes thereby causing the charged particles to migrate within and relative to the suspending medium. The velocity of each particle per unit electric field strength as expressed in microns/sec per volt/cm is referred to as the electrophoretic mobility of the particle and is designated by the letter u. zeta potential may be calculated from the expression: $\zeta = 36\ u(\eta/\epsilon)$ \hfill (1)

where:

$\zeta$ = zeta potential (millivolts)
$u$ = electrophoretic mobility (microns/sec per volt/cm)
$\eta$ = viscosity (poise)
$\epsilon$ = dielectric constant Since at a given temperature, $\eta$ and $\epsilon$ are constant, expression (1) may be rewritten as:

$\zeta = Ku$ \hfill (2)

where K equals 14.1 for an aqueous solution ($H_2O$) at 20° C.

Thus, zeta potential is an indication of the electrophoretic mobility of the particles, which, in turn, is an indication of the velocity with which the particles pass through the suspending medium under the influence of an applied electrical field.

Typically, apparatus for measuring electrophoretic mobility comprises an optically clear vessel defining a chamber, a pair of spaced electrodes supported by the vessel for impressing an electric field upon a sample medium in the chamber, a light beam for illuminating the sample medium contained in the chamber, and a microscope for viewing the migration of particles relative to the medium in the chamber when a voltage is impressed across the electrodes. Making measurements of electrophoretic mobility or zeta potential via such apparatus is often referred to as microelectrophoresis whereas the optically clear vessel employed with such apparatus is often referred to as an electrophoresis chamber or cell.

Prior art microelectrophoresis apparatus may usually be classified as "manually operated" or "semi-automatic". In the "manually operated" microelectrophoresis apparatus, such as that disclosed for example, in the patent to Riddick, No. 3,454,487, the eyepiece of the microscope includes an ocular micrometer or distance scale and electrophoretic mobility must first be measured by timing the migration or traverse of a single observed particle between gradations on the distance scale with a stop watch, and then employing this information to separately calculate zeta potential from either expressions (1) or (2) above. It is apparent that the manually operated apparatus requires many such repeated operations to accurately determine the zeta potential of the particles in a sample bulk medium and therefore it is time consuming and tedious to employ. Moreover, the electrophoresis chamber employed in the Riddick type "manually operated" apparatus has a cylindrically shaped cross section thus making it more difficult than is otherwise desirable to focus the microscope objective precisely on the stationary layer of the chamber. As is well known in this art, the term "stationary layer" refers to an imaginary surface passing through the chamber and which defines the locus of zero velocity with regard to the suspending medium and electro-osmotic phenomena, i.e., when electrophoretic mobility is measured on this surface or stationary layer as it is called, compensation does not have to be made for a velocity component imparted to the suspending medium due to the effects of electro-osmosis.

In order to facilitate more rapid and efficient measurements of electrophoretic mobility, attempts were made to develop a "semi-automatic" microelectrophoresis apparatus as disclosed, for example, in the patent to Greenwood et al, No. 3,764,512. In the latter apparatus, a coherent light beam from a laser is caused to intermittently scan a path located on the stationary layer of an electrophoresis chamber by means of a mirror galvanometer at a rate equal to the migration rate of the particles in the chamber. The operator merely views the migrating particles in the chamber through a microscope and simultaneously adjusts the scanning rate of the mirror galvanometer by adjusting a potentiometer in the galvanometer control circuit until the scanning laser beam appears to visually track the migrating particles as viewed through the microscope. Via appropriate scaling circuitry interacting with the galvanometer drive circuit and the circuit supplying the voltage drop across the chamber a value for zeta potential or electrophoretic mobility may automatically be displayed through suitable means such as an electronically operated digital readout.

In still another form of "semi-automatic" microelectrophoresis instrument obtainable from Pen Kem, Inc. Croton-On-Hudson, New York, under the designation Model 102, means are provided for scanning the light image reflected from the migrating particles rather than scanning the laser illumination beam. That is, a galvanometer driven prism is located externally of the microscope between the microscope objective and the electrophoresis cell chamber to optically intercept the path of the reflected particle images, and the prism is intermittently scanned in a direction opposite to that of particle migration within the cell. Thus, the operator merely adjusts the galvanometer drive circuit until the apparent motion of the particles as viewed in the eyepiece of the microscope is zero i.e., the particles appear stationary, and the value of zeta potential or electrophoretic mobility corresponding to the particular voltage impressed across the electrophoresis chamber is then instantaneously and automatically displayed.

Although each of the foregoing "semi-automatic" microelectrophoresis instruments represents an improvement over the "manually operable" Riddick type instrument particularly as concerns the speed and efficiency of obtaining zeta potential measurements, the former instruments still suffer from certain disadvantages. For example, in both versions of the "semi-automatic" instrument described above, the electrophoresis chamber employed has a square shaped cross section, 5 or 6 mm on a side. Although a square or rectangular shaped cell facilitates focusing of the microscope objective on the stationary layer in the chamber, due to the chamber's relatively large cross-sectional area it is extremely susceptible to convection currents induced by thermal gradients resulting from the heat generated by the current passing between the electrodes in the chamber, the laser illumination beam incident upon the chamber, the proximity of the galvanometer drive coils to the chamber, and so on. Such convection currents impart velocity components to the sample medium in the cell which may result in significant errors in the measured electrophoretic mobility unless tedious efforts are taken to calibrate out the unwanted velocity components.

Against the foregoing background, it is a principal object of the present invention to provide an improved semi-automatic microelectrophoresis apparatus.

It is another object of the present invention to provide an improved semi-automatic microelectrophoresis apparatus that is rendered relatively impervious to thermodynamic transients induced within its electrophoresis cell and therefore which is capable of rendering more accurate measurements of zeta potential and electrophoretic mobility.

It is yet another object of the present invention to provide an improved electrophoresis chamber construction for use with a semi-automatic microelectrophoresis apparatus.

Toward the accomplishment of these and additional objects and advantages, the present invention, briefly summarized, comprises an electrophoresis chamber, circuit means for impressing a voltage across the chamber, means for generating a light beam to illuminate a portion of the chamber, and a microscope including an objective lens system and an eyepiece for viewing illuminated particles migrating relative to a suspending medium within the chamber under the influence of the applied voltage. Disposed within the microscope between the objective lens system and the eyepiece i.e., internally of the microscope, is a movable optical prism driven by a galvanometer, the drive circuit of which includes an adjustable potentiometer for controlling the rate and direction of movement of the optical prism. Circuit means connected to the galvanometer drive circuit and the circuit applying the voltage potential across the chamber is adapted to develop a signal proportional to the electrophoretic mobility or zeta potential of the migrating particles in the medium in the chamber when the rate of movement of the optical prism is adjusted such that it cancels the transfer velocity of the migrating particles and the particles appear stationary when observed through the eyepiece of the microscope. Because the movable optical prism is located internally of the microscope between the objective lens and the eyepiece, it is possible to employ an electrophoresis chamber having a rectangular cross-sectional shape such that the height dimension thereof is significantly reduced relative to the width dimension thereof. By virtue of this geometry the electrophoresis chamber is rendered relatively impervious to thermodynamic transients. The electrophoresis chamber which is constructed of three relatively thin flat plates furthermore includes means for mounting and supporting a pair of spaced electrodes; and moreover, includes means for avoiding entrapment of air bubbles when being filled with a sample bulk medium.

The foregoing and still other features and advantages as well as a more complete understanding of the present invention will be made apparent from a study of the following detailed description of the invention in connection with the accompanying drawings wherein:

FIG. 2 is a plan view of the electrophoresis chamber employed with the microelectrophoresis apparatus of the present invention;

FIG. 3 is a sectional view of the electrophoresis chamber of FIG. 2 taken along line 3—3 thereof;

FIG. 4 is a sectional view of the electrophoresis chamber of FIG. 2 taken along line 4—4 thereof;

Figure 8:
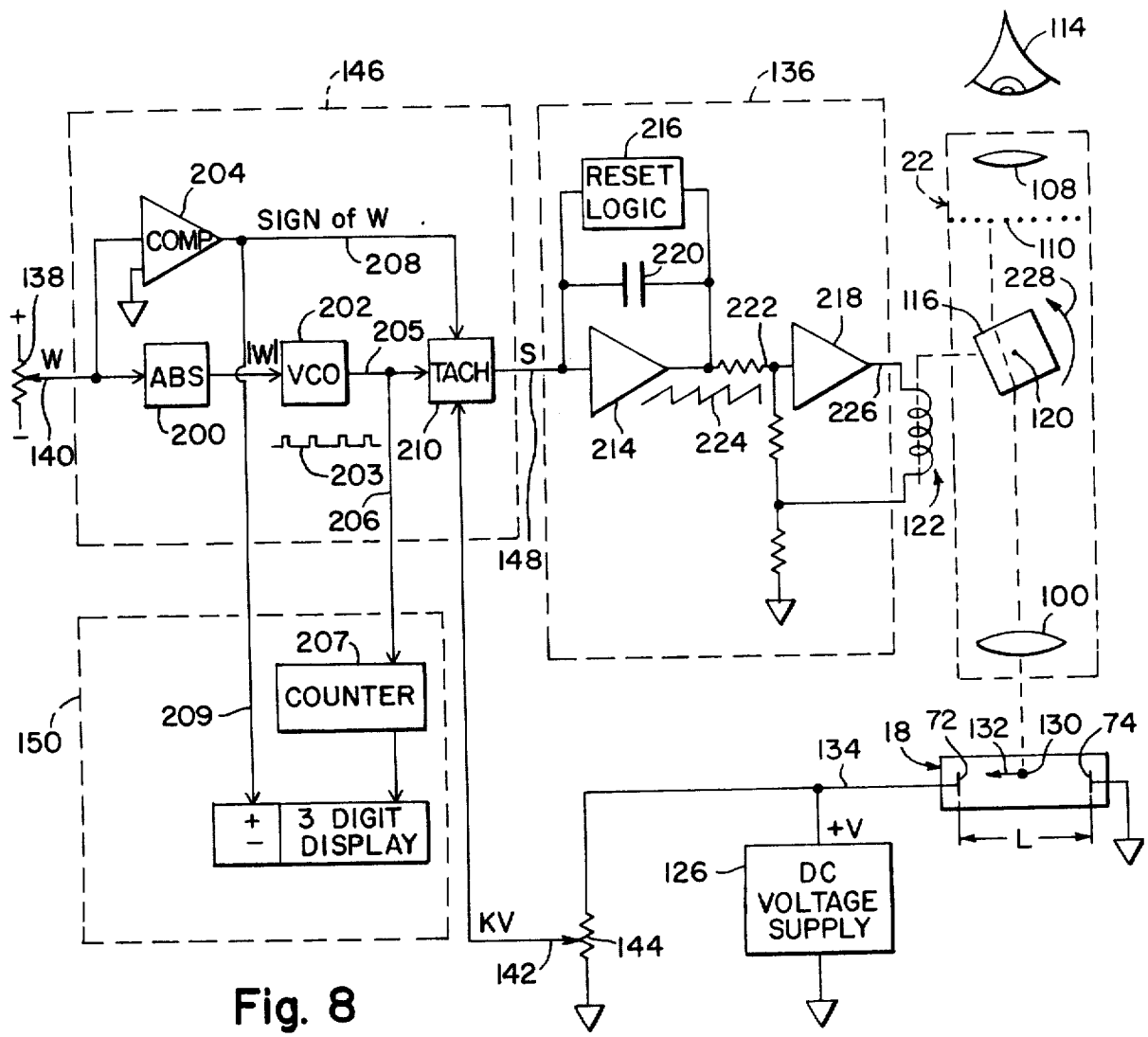

FIGS. 5, 6, and 7 are plan views of respective portions of the electrophoresis chamber of FIG. 2; and FIG. 8 is a schematic block diagram of the microelectrophoresis apparatus of the present invention.

Figure 1:
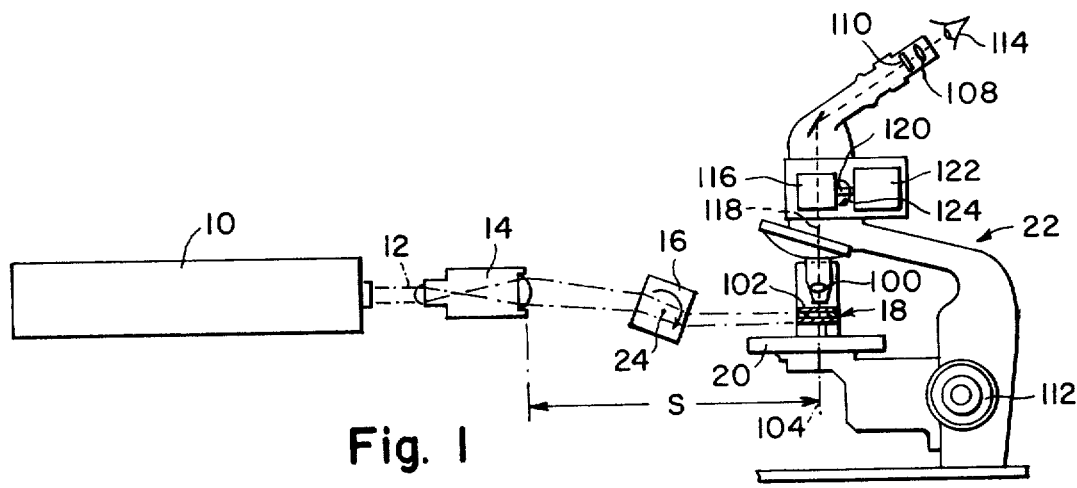
FIG. 1 is a schematic representation of the optical components of the microelectrophoresis apparatus of the present invention.

Referring now to FIG. 1, there is shown an illumination source 10 such as a helium neon laser capable of generating a well collimated coherent beam of light 12 essentially having a circular beam cross section. A helium neon laser found suitable for use with the apparatus of the present invention is the Model 133, obtained from Spectra-Physics, the latter being adapted to generate a 0.7 mm circular beam at a wavelength of 6328° A and at a power output of 2 mw.

Light beam 12 is caused to pass through beam expanding and focusing lens system 14 and beam height adjusting prism 16 before it passes through the optically transparent side wall of electrophoresis chamber or cell 18 supported on the stage 20 of microscope 22. By means of expanding and focusing lens system 14 whose construction and operation are well known, the coherent circular beam 12 is compressed in the vertical direction and brought to a focus at a distance "S" substantially as shown i.e., within the electrophoresis chamber 18 and coincidental with the optical axis of microscope 22. Inasmuch as the beam 12 has been vertically compressed, the illumination afforded by the focused beam 12 will be brightly concentrated in a relatively narrow vertical range thus facilitating dark field illumination of even extremely small sized particles suspended in a bulk medium contained within chamber 18. Beam expanding and focusing lens system 14 preferably is adapted to sufficiently compress beam 12 to form a focal spot at the distance "S" of the height of which (vertical dimension) is approximately no greater than the depth of field of focus of the objective lens system of microscope 22 so as to facilitate dark field illumination in the region of the stationary layer.

Beam height adjusting prism 16 preferably comprises a conventional square prism mounted for rotation about an axis passing through and perpendicular to the plane of FIG. 1 by suitable manually operable means (not shown). By rotating prism 16 about axis 24, the focal spot of beam 12 may be raised or lowered as necessary to precisely position the latter on the stationary layer within electrophoresis chamber 18, i.e., the region where electro-osmotic effects do not contribute any velocity components to the suspending medium within the chamber 18.

With reference to FIGS. 2–7, electrophoresis chamber 18 comprises a base portion 26 including a tubular passageway 28, and a pair of enclosures 30, 32 mounted on either opposed end of base portion 26, each of said enclosures defining a hollow cylindrically shaped sample receiving reservior 34, 36 respectively. Enclosure 34 includes an external hollow inlet tube 38 communicating with a passageway 40 located in the side wall of enclosure 30 which passageway, in turn, communicates with reservoir 34. Simiarly, an external hollow tube 42 communicates with a passageway 44 located in the roof of enclosure 32 which passageway communicates with reservoir 36. A stopper or cap 46 may be employed to seal off external tube 42 and thus reservoir 36 whereas a similar cap (not shown) may be employed to seal off external tube 38 and reservoir 34.

Reservoir 34 communicates with passageway 28 at one end thereof through a port or opening 48 whereas reservoir 36 communicates with passageway 28 at the other end thereof through a similar port or opening 50.

From the foregoing, it will be appreciated that a sample bulk medium containing suspended particles may be admitted through external inlet tube 38 and interconnecting passage 40 into reservoir 34, then through port 48, passageway 28, and finally through port 50 entering and filling reservoir 36. In this regard, it is noted that although the enclosure interior ceiling portion 52 defining reservoir 30 is substantially flat as viewed in FIG. 3 and interconnecting passage 40 is located in the enclosure side wall as mentioned above, in accordance with the present invention the corresponding enclosure interior ceiling portion 54 defining reservoir 36 is tapered in an upwardly converging manner e.g., it is conically shaped, with the interconnecting passageway 44 being located centrally at the apex of the cone in and extending through the roof portion of enclosure 32 as substantially shown. By this construction any air bubbles which might otherwise tend to collect and remain trapped interiorly of the chamber 18 when the latter is being filled with a bulk medium instead advantageously are urged to exit the chamber via the upwardly converging or conically shaped ceiling 54, interconnecting passageway 44 and external tube 42 by the hydraulic pressure of the bulk medium rising in reservior 36. Of course, when reservoir 36 has been completely filled with the bulk suspending medium as indicated by a slight efflux of the medium through the external tube 42, the latter may be sealed via cap 46.

The base portion 26 of electrophoresis chamber 18 comprises three flat, relatively thin, plates 56, 58, and 60 each preferably fabricated of an optically clear, reasonably stable material such as glass or methyl methacrylate. The base portion preferably includes a fourth plate like member 61 which, however, need not necessarily be optically clear (shown in FIG. 3 only).

Plate 56 includes a pair of spaced oblong shaped openings which serve as the ports 48 and 50 whereas plate 58 includes a relatively large central opening which serves as passageway 28. In addition, plate 56, plate 58, and plate 60 each include a pair of spaced circular openings 62, 64, and a plurality of small circular openings 66 disposed in a regular spaced manner adjacent the periphery thereof. The plates 56, 58, and 60 are coextensively superposed relative to each other in the sandwich like configuration shown in FIGS. 2–4. In this manner, not only do the spaced ports 48, 50 register with the opposed ends of passageway 28, but the spaced openings in each plate register with one another to form a pair of corresponding aligned holes extending through base portion 26 for receiving the lower or stem portions 68, 70 of a pair of electrodes 72, 74 each of which latter has a corresponding upper portion 73, 75 extending in upright fashion into reservoirs 34, 36 respectively. The smaller openings 66 adjacent the periphery of each plate 56, 58, and 60 also register relative to each other to serve as through holes for receiving a corresponding plurality of threaded fasteners or the like (not shown) for firmly and securely fastening the plates and the enclosures together substantially in the arrangement of FIGS. 2–4. It will be understood that bottom plate member 61 also includes similar spaced holes 62, 64, and 66. In addition, plate member 61 preferably includes a pair of spaced counterbores 76, 78 for receiving and enclosing a pair of electrical terminals in the form of conductive disks 80, 82 suitably fastened to the distal ends of electrode stem portions 68, 70 respectively as, for example, by means of a screw fastener element threaded into a tapped hole within the distal end of each electrode stem portion 68, 70 respectively. Electrical conductors 84, 86 are connected to the usual power supply 126 (FIG. 8) for impressing a voltage across electrodes 72, 74.

As is well known in the art, in order to minimize the emission of gas bubbles during operation, electrode 72 which serves as an anode preferably is fabricated of molybdenum whereas electrode 74 which serves as a cathode preferably is fabricated of platinum.

Turning again to FIG. 1, electrophoresis chamber 18 is positioned horizontally on the stage 20 of microscope 22 such that the longitudinal axis of the chamber extends into the plane of the paper perpendicular thereto as viewed in FIG. 1 and the objective lens system 100 of the microscope is positioned directly over the upper surface 102 of the chamber 18 with the optical axis 104 of the objective lens system passing substantially centrally through passageway 28 (FIG. 3) perpendicular thereto. The position of the objective lens with regard to upper surface 102 also is schematically indicated in FIG. 2 by the broken line circle 106. By this arrangement, and by virtue of the optically clear nature of plate 56, the objective lens system has a clear field of view within passageway 28.

In addition to objective lens system 100, microscope 22 has an eyepiece or ocular lens system 108 preferably including a reticle or ruled reference grid 110, and the usual focusing control 112. Operation of the focusing control 112 causes up and down movement of microscope stage 20 relative to the microscope lens system thereby varying the working distance between the objective lens system 100 and the electrophoresis chamber 18. Thus, by suitable manipulation of this focus control 112, an observer at 114 may visually focus the lens system of the microscope upon the stationary layer or plane of zero electroosmotic velocity passing through passageway 28 of chamber 18.

In accordance with the present invention, a scanning optical prism 116, which preferably is a square prism is mounted internally of microscope 22 in such a manner as to intercept the optical path 118 of the microscope between the objective lens system 100 and the eyepiece lens system 108. Prism 116 is supported on a suitably rotatable shaft 120 the axis of which lies in the plane of FIG. 1 and extends substantially perpendicular to optical path 118 of the microscope. Coupled to rotatable shaft 120 is a conventional galvanometer 122 which in response to a suitable drive current is adapted to rotate shaft 120 and therefore prism 116 about the axis defined by shaft 120 as indicated by the arrow 124. As will be explained in more detail in the ensuing discussion, during operation the optical prism 116 actually is rotated via shaft 120 through a predetermined arc e.g., ±.1 radians, at a rate proportional to and in a direction opposite to that of the actual velocity of particles migrating within passageway 28 of electrophoresis chamber 18 under the influence of a preselected voltage impressed across electrodes 72, 74.

In any event, location of scanning prism 116 internally of the microscope so as to intercept the optical axis of the microscope between the objective lens system 100 and the eyepiece lens system 108 advantageously facilitates employment of a rectangularly shaped electrophoresis chamber having a reduced height dimension relative to its transverse width dimension or as best seen from FIGS. 2 and 4 an electrophoresis chamber having a rectangular cross-sectional shape where the dimension "a" is significantly larger than the dimension "b". Extremely satisfactory results have been achieved when "b" is equal to 1.5 mm and "a" is equal to 15 mm ($a/b = 10$). Electrophoresis chambers of the foregoing geometrical configuration (sometimes referred to as "flat" chambers) are generally less susceptible to thermodynamic transients in the form of convection currents arising primarily from heat generated by the electric current passing between the electrodes in the chamber and therefore are capable of yielding more accurate electrophoretic mobility measurements than the prior art chamber having a square shaped cross section 5 6 mm on a side.

It will be appreciated that the slope of the electroosmotic velocity profile in "flat" chambers becomes steeper as the ratio a/b is increased. Accordingly, it is desirable that the depth of field of focus of the microscope objective lens system be made as shallow as possible. The latter may be facilitated by increasing the magnification or the numerical aperture (N.A.) of the microscope objective lens system and decreasing the working distance between the objective lens system and the upper surface of the electrophoresis chamber. By way of example excellent results have been achieved employing a Nikon Model SU microscope modified to include the scanning optical prism 116 and galvanometer 122 internally thereof so as to intercept the optical path between its objective lens system and its eyepiece lens system. The scanning prism is 30 mm on a side and capable of being scanned to produced an equivalent particle displacement of 70μm per scan. In Table I below are set forth the optical constants of this microscope in comparison to those of the prior art microelectrophoresis instrument:

TABLE I

| MICROSCOPE OPTICAL CONSTANTS | | |
| --- | --- | --- |
| ITEM | Present Invention | Prior Art Microelectrophoresis Instrument (Pen Kem, Inc. - Model 102) |
| Overall Field of View Within Chamber | 650μm | 1250μm |
| Objective Magnification | 27 | 7 |
| Numerical Aperature of the Objective | .4 | .22 |
| Depth of Field of Focus | 5μ | 21μ |
| Working Distance | 5.7 mm | 14 mm |
| Eyepiece Magnification | 10 | 20 |
| Overall Magnification | 270 | 140 |
| Chamber Geometry | Rectangular 1.5 mm × 15 mm | Square 6 mm × 6 mm |

It will be noted from Table I that the working distance of the microscope of a preferred form of the present invention is only 5.7 mm, however, this is still quite adequate to enable an operator to observe particles in focus at the top and at the bottom of the electrophoresis chamber, an important advantage when it is desired to construct velocity profiles of a particular bulk medium in the chamber by measuring the electrophoretic mobility of the particles suspended therein at a plurality of different heights within the chamber.

Turning now to FIG. 8 the operation of the microelectrophoresis apparatus of the present invention now will be described. For purposes of this portion of the description it is assumed that the electrophoresis chamber 18 has been filled with a bulk medium having particles dispersed therein and positioned relative to the stage 20 of microscope 22 as schematically indicated in FIGS. 1 and 8 with the laser beam 12 illuminating the chamber 18 in the region of the latter's stationary layer and the field of view of the microscope objective lens system. Furthermore, it is assumed that a D.C. voltage potential obtained from D.C. voltage supply 126 is impressed across the electrodes 72, 74 causing a net electronegatively charged particle 130 suspended in the bulk medium to migrate toward the anode electrode 72 as indicated in FIG. 8 by arrow 132 and that the operator-observer at 114 has adjusted the focus control 112 to focus the microscope objective on the stationary layer of chamber 18.

The motion of particle 130 seen by the observer in the plane of the reticle 110 consists of two velocity components. The first velocity component $V_e$ is due to the electrophoretic movement of the particle as magnified by the microscope objective 100. the second velocity component $V_p$ is a translation of the particle image caused by the rotation or scanning motion of the prism 116 about the axis of shaft 120. A quantitative description of these two velocity components of the image movement of particle 130 may be given as follows.

The electrophoretic velocity of the particle 130 is equal to its mobility $\mu$ times the electrical field strength E. In turn, E may be expressed as V/L where V is the voltage made available by voltage supply 126 on conductor 134 and being applied across the electrodes 72, 74, and L designates the effective length of the chamber or approximately the linear spacing between electrodes 72, 74. If the magnification of the objective lens is M, the image velocity due to the electrophoretic effect is simply M times the electrophoretic velocity or $$V_e = Mu\ V/L \quad (3)$$

On the other hand, the velocity component due to the prism rotation may be approximated as:

$$V_p = t\left(\frac{N-1}{N}\right)\dot{\theta} \quad (4)$$

where $\tau$ is the thickness of the prism, N is the prism's index of refraction, and $\dot{\Theta}$ the rotation rate of the prism about the axis of shaft 120 in radians/sec, and the prism rotation causes relatively slight angular deviations between the normal to the prism's incident surface and the optical path of the microscope.

The rotation rate of prism 116 may also be expressed as $$\dot{\theta} = k_g S \quad (5)$$

where kg is the scale factor associated with the galvanometer 122 and the galvanometer drive circuit indicated by the broken line block 136 and $$S = KVW \quad (6)$$

where W is equal to the voltage output of operator controlled adjustable potentiometer 138 appearing on sliding arm 140, and KV is the voltage V from D.C. supply 126 via line 134 across adjustable calibration potentiometer 144. In electrical terms S is equal to the average current in conductor 148 which signal comprises the output of a multiplier network indicated by the broken line block 146.

Substituting (5) and (6) into (4) yields:

$$V_p = t\left(\frac{N-1}{N}\right)\dot{\theta} = t\left(\frac{N-1}{N}\right)k_s \quad (7)$$

In order to make a measurement the operator merely adjusts the sliding arm 140 of potentiometer 138 in such a manner that the image motion caused by the electrophoretic effect is just cancelled by an opposite motion produced by the prism rotation. At this null condition the particle image appears stationary reference to the eyepiece reticle of the microscope and $V_e = V_p$. Stated otherwise $$Mu\ V/L = t\left(\frac{N-1}{N}\right)k_s KVW \quad (8)$$

or $$u = \left[t\left(\frac{N-1}{N}\right)k_s \frac{KL}{M}\right]W \quad (9)$$

From expression (9) it is seen that the electrophoretic mobility, i.e., the quantity being measured, is directly proportional to W the output voltage of potentiometer 138 and that all of the parameters inside the brackets can be considered as constants. Hence, by means of the digital voltmeter, indicated by the broken line block 150, connected through multiplier network 146 to the output arm 140 of adjustable potentiometer 138, the voltage W may be displayed thereby directly indicating electrophoretic mobility provided the operator has adjusted the sliding arm 140 of potentiometer 138 to satisfy the null conditions of expressions (8) and (9). These null conditions are satisfied, of course, when the scanning rate of the prism 116 produces an apparent image the scanning rate of the prrism 116 produces an apparent image motion equal to and opposite in direction to the electrophoretic velocity of the suspended particle 130 as viewed by the operator through the microscope eyepiece.

In order to more fully appreciate the operation of the circuit means of FIG. 8, assume that the operator at 114 observes a net movement of particle 130 toward the anode 72 in the direction of arrow 132 and that the sliding arm 140 of potentiometer 138 is positioned at the center of its winding corresponding to the condition W equal to zero volts. The operator will then adjust the sliding arm 140 of the potentiometer 138 until he visually observes that the particle image as viewed through the microscope has become stationary. Before this can occur, however, the operator must move the sliding arm 140 of the adjustable potentiometer 138 toward the negative terminal of the potentiometer winding to develop a voltage W on line 140 of negative polarity. This signal containing both magnitude and sign information is applied simultaneously to the absolute value circuit 200 and the comparator circuit 204. The absolute value circuit 200 produces an output signal $|W|$ which is applied to a linear voltage controlled oscillator 202 which, in turn, produces an output signal on line 205 in the form of a train of pulses 203 whose repetition rate or frequency is proportional to $|W|$. Pulse train 203 is also applied via conductor 206 to counter 207 of digital voltmeter 150. At the same time, comparator circuit 204, which may comprise, for example, an operational amplifier without any feedback between its output and input, generates a logic signal corresponding to the SIGN or polarity of W on line 208 and simultaneously applies this signal to the sign indicator of digital voltmeter 150 by way of conductor 209. A tachometer circuit 210 receives as inputs the pulse train signal 203 whose frequency is proportional to $|W|$ (line 205), the SIGN of W signal (line 208) and the signal proportional to KV (line 142) and in response thereto produces an output signal conductor 148 comprising a train of fixed width current pulses, whose magnitude is proportional to KV and whose polarity is determined by the SIGN of W. Since the current pulse width is constant, the average current is proportional to the frequency of the output signal of voltage controlled oscillator 202 (pulse train 203). Thus the output signal on line 148 is S = KVW as required from (6) above.

The current signal S is then applied to the galvanometer drive circuit 136. The latter consists of a low drift integrator coupled to a voltage to current convertor to drive the galvanometer 122. The integrator consists of an operational amplifier 214 with a capacitive feedback loop. A reset circuit 216 is provided in parallel to feedback capacitor 220 so as to assure that the galvanometer is always kept within $\pm.1$ radian limits necessary to avoid nonlinearities in the angular response of the galvanometer coil. The reset logic sets the integrator to the one limit whenever it approaches the other. As a result a sawtooth waveform 220 whose frequency is directly proportional to the electrophoretic mobility of particle 130 and the voltage applied across electrodes 72, 74 of chamber 18 (e.g., 0.14 hz at $u = \pm 1.0$, and V = 100 v) appears on line 222 at the output of the integrator. Signal 220 is applied to an output amplifier 224 which provides a galvanometer drive current on line 226 proportional to the output of the integrator i.e., sawtooth waveform 220.

It is thus seen that the optical prism 116 in response to signal 220 will be scanned in the direction of arrow 228, quickly reset to its original position, be scanned again, and so on. Inasmuch as the operator has already created the null condition required to solve equations (8) and (9) by adjusting the sliding arm 140 of potentiometer 138 in the desired direction, the rate of scan of the prism 116 will comprise that necessary to produce an apparent image velocity equal to the electrophoretic velocity of particle 130 and the direction of scan will be opposite to that of the observed particle image i.e., counter clockwise about axis 120 as viewed in FIG. 8. The digital voltmeter thus automatically displays the sign and magnitude of electrophoretic mobility in accordance with (9) above. In connection with the latter it will be noted that the scale factor i.e., the bracketed term in expression (9) above, is independent of the voltage V applied across chamber 18. This is extremely desirable since it is often necessary to change the voltage potential across the chamber over a relatively wide range for different bulk mediums having dispersed particles therein. Thus, it will be understood that voltage supply 126 in FIG. 8 preferably is adjustable so as to be able to supply a range of selectable voltages to be impressed across the chamber 18 e.g., 0-400 v.

Finally, it will be noted that calibration of the circuit of FIG. 8 is readily accomplished by adjustment of calibration potentiometer 212 which in turn changes the value of K. As is known in the art, a similar calibration means may be employed to convert the reading displayed by digital voltmeter 150 from electrophoretic mobility to zeta potential.

Thus, although a preferred embodiment of the present invention has been disclosed in detail above as required by statute, many variations and modifications thereof will occur to those skilled in the art. Accordingly, the present invention should be limited only by the true spirit and scope of the appended claims.

I claim:

1. Apparatus for measuring the electrophoretic mobility of particles migrating in a suspending medium under the influence of an applied electric field comprising:
   an electrophoresis chamber,
   a microscope having an objective lens system and an ocular lens system, said microscope being positioned to view said chamber along an optical path extending from said chamber through said objective lens system toward said ocular lens system,
   optical means associated with said microscope to intercept said optical path between said chamber and said ocular lens system,
   means for scanning said optical means relative to said optical path, and means coupled to said scanning means for controlling the scanning of said optical means wherein the improvement comprises disposing said optical means relative to said microscope such that said optical means intercepts said optical path between said objective lens system and said ocular lens system.

2. The apparatus of claim 1 wherein said microscope includes a housing and said optical means is disposed interiorly of said housing between said objective lens system and said ocular lens system.

3. The apparatus of claim 2 wherein said optical means comprises an optical prism mounted for rotation in said housing.

4. The apparatus of claim 1 wherein said means coupled to said scanning means for controlling the scanning of said optical means includes manually operable control means and circuit means connected between said scanning means and said control means.

5. The apparatus of claim 4 including display means, said display means being coupled to said circuit means and being responsive thereto for indicating the electrophoretic mobility or zeta potential of particles migrating in said cell when said control means is adjusted to cause said scanning means to scan said optical means such that the migrating particles in said chamber appear stationary when viewed through said ocular lens system of said microscope.

6. The apparatus of claim 4 wherein said scanning means comprises a galvanometer.

7. The apparatus of claim 4 wherein said manually operable control means comprises an adjustable potentiometer.

8. The apparatus of claim 1 including adjustable voltage supply means connected to said electrophoresis chamber for producing an electrical field within said chamber.

9. The apparatus of claim 1 including means for directing a light beam through said electrophoresis chamber for illuminating said chamber in the region of its stationary layer.

10. The apparatus of claim 9 wherein said means for directing said light beam comprises a laser.

11. The apparatus of claim 10 further including a lens system between said laser and said chamber for compressing the light beam from said laser and focusing said compressed light beam in region of said stationary layer.

12. The apparatus of claim 1 wherein said electrophoresis chamber has a rectangular cross section, the transverse width dimension of said rectangular cross-section being substantially greater than the transverse height dimension thereof.

13. The apparatus of claim 12 wherein the ratio of said width dimension to said height dimension is about 10:1.

14. The apparatus of claim 1 wherein said electrophoresis chamber comprises a base member defining a tubular passage, a pair of sample receiving enclosures on said base member, each one of said pair of enclosures being disposed adjacent a respective end of said tubular passage, a pair of openings in said base member, one of said pair of openings connecting the interior of one of said enclosures to one end of said tubular passage, the other of said pair of openings connecting the interior of the other of said enclosures to the other end of said tubular passage, and a pair of electrodes fixedly supported on said base member, one of said pair of electrodes extending into the interior of one of said enclosures adjacent said one of said pair of openings, the other of said pair of electrodes extending into the interior of said other enclosure adjacent said other of said pair of openings, and means for admitting a sample bulk medium into one of said enclosures.

15. The apparatus of claim 14 wherein said tubular passage has a rectangular cross-sectional shape, the transverse width dimension of said rectangular cross-sectional shape being substantially greater than the transverse height dimension thereof.

16. The apparatus of claim 15 wherein the ratio of said width dimension to said height dimension is about 10:1.

17. The apparatus of claim 14 wherein said base member comprises first, second, and thrid plate members coextensively superposed relative to each other, said pair of openings being disposed in said first plate member, and said second plate member having a central opening therein to define said tubular passage.

18. The apparatus of claim 17 wherein at least said first and second plate members are optically transparent.

19. The apparatus of claim 17 wherein said first, second, and third plate members each include a pair of spaced openings therein, corresponding ones of said pair of openings in said plate members being aligned to receive one of said electrodes respectively.

20. The apparatus of claim 14 wherein the other of said enclosures includes means for permitting the escape of air bubbles therefrom when said enclosures and said tubular passage are being filled with a sample bulk medium.

21. The apparatus of claim 20 wherein said means for permitting the escape of air bubbles comprises an upwardly converging ceiling internally of said other enclosure, and an opening extending between said ceiling portion and the exterior of said other enclosure.

22. The apparatus of claim 21 wherein said ceiling portion is conically shaped, and said opening extends between the apex thereof and the exterior of said other enclosure through the roof of said other enclosure.

23. For use in electrophoresis apparatus an electrophoresis chamber comprising: a base member defining a tubular passage, a pair of sample receiving enclosures being on said base member, each one of said pair of enclosures being disposed adjacent a respective end of said tubular passage, a pair of openings in said base member, one of said pair of openings connecting the interior of one of said enclosures to one end of said tubular passage, the other of said pair of openings connecting the interior of the other of said enclosures to the other end of said tubular passage, and a pair of electrodes fixedly supported on said base member, one of said pair of electrodes extending into the interior of one of said enclosures adjacent said one of said pair of openings, the other of said pair of electrodes extending into the interior of said other enclosure adjacent said other of said pair of openings, means associated with said one of said enclosures for admitting a sample bulk medium into said one of said enclosures and wherein the other of said enclosures includes means for permitting the automatic escape of air bubbles therefrom when said enclosures and said tubular passage are being filled with a sample bulk medium through said sample admitting means.

24. The apparatus of claim 23 wherein said tubular passage has a rectangular cross-sectional shape, the transverse width dimension of said rectangular cross-sectional shape being substantially greater than the transverse height dimension thereof.

25. The apparatus of claim 24 wherein the ratio of said width dimension to said height dimension is about 10:1.

26. The apparatus of claim 23 wherein said base member comprises first, second, and third plate members coextensively superposed relative to each other, said pair of openings being disposed in said first plate member, and said second plate member having a central opening therein to define said tubular passage.

27. The apparatus of claim 26 wherein at least said first and second plate members are optically transparent.

28. The apparatus of claim 26 wherein said first, second, and third plate members each include a pair of spaced openings therein, corresponding ones of said pair of openings in said plate members being aligned to receive one of said electrodes respectively.

29. The apparatus of claim 23 wherein said means for permitting the escape of air bubbles comprises an upwardly converging ceiling internally of said other enclosure, and an opening extending between said ceiling portion and the exterior of said other enclosure.

30. The apparatus of claim 29 wherein said ceiling portion is conically shaped, and said opening extends between the apex thereof and the exterior of said other enclosure through the roof of said other enclosure.

* * * * *